US011613562B2

(12) United States Patent
Dasgupta

(10) Patent No.: US 11,613,562 B2
(45) Date of Patent: Mar. 28, 2023

(54) SARS-COV2 SPIKE PEPTIDES THAT INTERACT WITH HLA-DR1 AND HUMAN TLR8

(71) Applicant: Subhajit Dasgupta, Charleston, SC (US)

(72) Inventor: Subhajit Dasgupta, Charleston, SC (US)

( * ) Notice: Subject to any disclaimer, the term of this patent is extended or adjusted under 35 U.S.C. 154(b) by 1 day.

(21) Appl. No.: 17/346,245

(22) Filed: Jun. 13, 2021

(65) Prior Publication Data

US 2022/0098245 A1 Mar. 31, 2022

Related U.S. Application Data

(60) Provisional application No. 63/085,786, filed on Sep. 30, 2020.

(51) Int. Cl.
*C07K 14/165* (2006.01)

(52) U.S. Cl.
CPC ........ *C07K 14/165* (2013.01); *C07K 2317/33* (2013.01)

(58) Field of Classification Search
None
See application file for complete search history.

(56) References Cited

U.S. PATENT DOCUMENTS 11,376,320 B2 * 7/2022 Cho ...................... A61K 39/12

FOREIGN PATENT DOCUMENTS

CN 113754740 A * 12/2021

* cited by examiner

*Primary Examiner* — Nicole Kinsey White

(57) ABSTRACT

The multi-epitope SARS-COV2 Spike peptides are analyzed for their ability to form association or binding complex with HLA-DR1 and human TLR8 by using computer modeling and molecular docking experiments. These peptides are identified as candidates for vaccine development as well as antibody-based immunotherapy.

2 Claims, 12 Drawing Sheets

Figure 1:
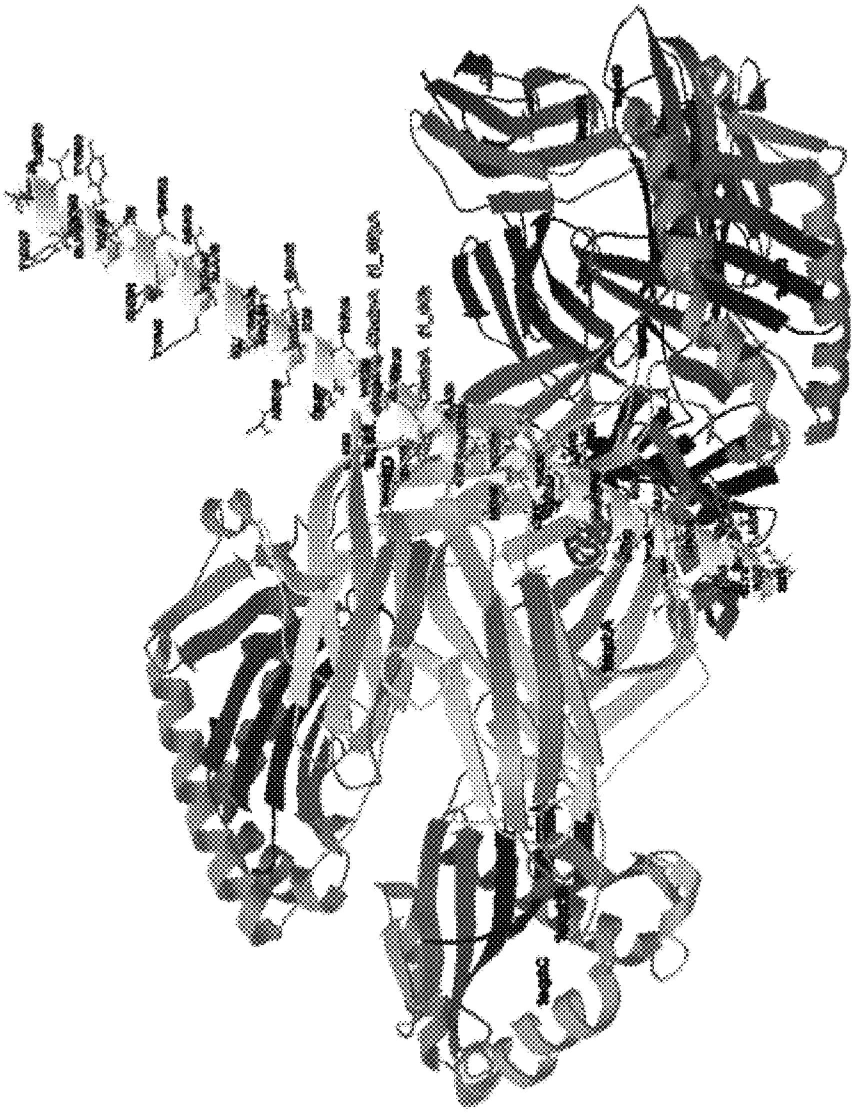

Specification includes a Sequence Listing.

SARS-COV2 SPIKE PEPTIDES THAT INTERACT WITH HLA-DR1 AND HUMAN TLR8

CROSS-REFERENCE TO RELATED APPLICATIONS

The recent pandemic causing Severe Acute Respiratory Syndrome Corona Virus 2 (SARS-COV2) is still a threat to world human population as virus related morbidity is still pervading in distinct parts of world. Several published materials are searched in NCBI (PubMed.gov), EBSCO and Google Scholar confining November 2019 to September 2020. Different investigators proposed importance of SARS-COV2 Spike glycoprotein in establishment of infection. The laboratories demonstrated Spike glycoprotein as ligand which is attached with Angiotensin Converting Enzyme 2 (ACE2) thus take entry into human cells.

The key words used to search cross references are: 1. SARS-COV2 and Spike glycoprotein; 2. COVID19 and Spike glycoprotein; 3. SARS-COV2 and Spike glycoprotein and HLA; 4. COVID19 and Spike glycoprotein and HLA; 5. SARS-COV2 and Spike glycoprotein and TLR8; 6. COVID19 and Spike glycoprotein and TLR8.

A few publications report Spike receptor binding domain (RBD) for ACE2. A few recent publications proposed viral epitopes from Spike, Envelop and Matrix protein components. But the peptide sequences they proposed are quite different with no match with the epitope sequences proposed in this Provisional patent file to USPTO from NeuroDrug Research LLC. Charleston, S.C.

However, all published contemporary references are listed in the Cross-Reference section as important research close to the area of this proposed invention but there is no similarity in proposed peptide sequences or vaccine candidate documents. The list of cross references is attached.

1. Basit A, Ali T, Rehman S U. Truncated human angiotensin converting enzyme 2; a potential inhibitor of SARS-CoV-2 spike glycoprotein and potent COVID-19 therapeutic agent. J Biomol Struct Dyn. 2020:1-10.
2. Bortolotti D, Gentili V, Rizzo S, Rotola A, Rizzo R. SARS-CoV-2 Spike 1 Protein Controls Natural Killer Cell Activation via the HLA-E/NKG2A Pathway. Cells. 2020; 9(9).
3. Dey A, Sen S, Maulik U. Unveiling COVID-19-associated organ-specific cell types and cell-specific pathway cascade. Brief Bioinform. 2020.
4. Grant O C, Montgomery D, Ito K, Woods R J. Analysis of the SARS-CoV-2 spike protein glycan shield reveals implications for immune recognition. Sci Rep. 2020; 10(1):14991.
5. Khalid Z, Naveed H. Identification of destabilizing SNPs in SARS-CoV2-ACE2 protein and spike glycoprotein: implications for virus entry mechanisms. J Biomol Struct Dyn. 2020:1-11.
6. Lan J, Ge J, Yu J, Shan S, Zhou H, Fan S, et al. Structure of the SARS-CoV-2 spike receptor-binding domain bound to the ACE2 receptor. Nature. 2020; 581(7807):215-20.
7. Mahapatra S R, Sahoo S, Dehury B, Raina V, Patro S, Misra N, et al. Designing an efficient multi-epitope vaccine displaying interactions with diverse HLA molecules for an efficient humoral and cellular immune response to prevent COVID-19 infection. Expert Rev Vaccines. 2020: 1-15.
8. Mittal A, Manjunath K, Ranj an RK, Kaushik S, Kumar S, Verma V. COVID-19 pandemic: Insights into structure, function, and hACE2 receptor recognition by SARS-CoV-2. PLoS Pathog. 2020; 16(8):e1008762.
9. Naz A, Shahid F, Butt T T, Awan F M, Ali A, Malik A. Designing Multi-Epitope Vaccines to Combat Emerging Coronavirus Disease 2019 (COVID-19) by Employing Immuno-Informatics Approach. Front Immunol. 2020; 11:1663.
10. Othman H, Bouslama Z, Brandenburg J T, da Rocha J, Hamdi Y, Ghedira K, et al. Interaction of the spike protein RBD from SARS-CoV-2 with ACE2: Similarity with SARS-CoV, hot-spot analysis and effect of the receptor polymorphism. Biochem Biophys Res Commun. 2020; 527(3):702-8.
11. Shang J, Ye G, Shi K, Wan Y, Luo C, Aihara H, et al. Structural basis of receptor recognition by SARS-CoV-2. Nature. 2020; 581(7807):221-4.
12. Sharifkashani S, Bafrani M A, Khaboushan A S, Pirzadeh M, Kheirandish A, Yavarpour Bali H, et al. Angiotensin-converting enzyme 2 (ACE2) receptor and SARS-CoV-2: Potential therapeutic targeting. Eur J Pharmacol. 2020; 884:173455.
13. Srivastava S, Verma S, Kamthania M, Kaur R, Badyal R K, Saxena A K, et al. Structural Basis for Designing Multiepitope Vaccines Against COVID-19 Infection: In Silico Vaccine Design and Validation. JMIR Bioinform Biotech. 2020; 1(1):e19371.
14. Stamatakis G, Samiotaki M, Mpakali A, Panayotou G, Stratikos E. Generation of SARS-CoV-2 S1 Spike Glycoprotein Putative Antigenic Epitopes in Vitro by Intracellular Aminopeptidases. J Proteome Res. 2020.
15. Tahir U I Qamar M, Shahid F, Aslam S, Ashfaq U A, Aslam S, Fatima I, et al. Reverse vaccinology assisted designing of multiepitope-based subunit vaccine against SARS-CoV-2. Infect Dis Poverty. 2020; 9(1):132.
16. Zheng Z, Monteil V M, Maurer-Stroh S, Yew C W, Leong C, Mohd-Ismail N K, et al. Monoclonal antibodies for the S2 subunit of spike of SARS-CoV-1 cross-react with the newly emerged SARS-CoV-2. Euro Surveill. 2020; 25(28).

STATEMENT OF FEDERALLY SPONSORED RESEARCH OR DEVELOPMENT

Not applicable.

This proposed invention research is not funded yet by any Federally sponsored Research Development. Or not even by any private organization. A NIH grant application has been submitted for fund to initiate exploratory research on SARS-COV2 vaccine development and determining immunotherapy.

THE NAMES OF THE PARTIES TO A JOINT RESEARCH AGREEMENT

Not applicable.

INCORPORATION-BY-REFERENCE OF MATERIAL SUBMITTED ON A READ-ONLY OPTICAL DISC OR AS TEXT FILE VIA THE OFFICE ELECTRONIC FILING SYSTEM

Reference to a Sequence Listing

The text file of amino acid sequences is submitted electronically.

The Specification section with proposed SARS-COV2 Spike peptide epitope sequences and detailed experiments are uploaded as part of electronic submission.

STATEMENT REGARDING PRIOR DISCLOSURES BY THE INVENTOR OR A JOINT INVENTOR

Not applicable.

BACKGROUND OF THE INVENTION

Recent pandemic causing SARS-COV2 takes route through nostrils to upper respiratory tract and gradually enters into trachea to lower respiratory tract involves lung. The respiratory route expresses angiotensin converting enzyme 2 (ACE2) which are known to act as receptor for the virus. The first step of SARS-COV2 infection is to attach with human cells and inject its single stranded positive sense RNA genome into host cell cytoplasm for replication to generate next generation virions to infect new cells killing the cells within which they grow. The reason of this virus induced cytopathic effect, petechiae are found which under extensive viral growth can coalesce to form patchy skin rash. The shortening of breath with dry cough worsens the clinical condition lead unattended patients to death. The infection spreads fast through droplets by sneezing and coughing primarily. In order to control the fast spread of infection, choice of mechanical separation of population in community and set up barrier to limit droplets with heightened sanitation come first as part of epidemiology directed prevention of contagious infection. The obvious second important choice is to identify route and mechanism of establishment of infection, which is critical to develop vaccine, immunotherapy or anti-SARS-COV2 drug. As found, still there is no approved vaccine for the virus in market. However, an RNA vaccine clinical trial is currently going on with little success.

The literature survey of last 10 years including last 11 months of pandemic period demonstrated the virus SARS-COV2 uses their Spike glycoprotein (S protein) to anchor onto ACE2. Still today no other host cell receptor has been detected for entry of the virus. The observations from infected patients show elevated immunoglobulin M and G levels with expression of different cytokines like, IL 1b, TNF alpha, MCP1, GMCSF, IFN gamma, IL10, IL6, IL8 at various extent (PMID 32460144). The surge of cytokine expression though indicates a possibility of immune system inability to detect specific viral antigenic epitope, the phenomena also indicate towards feasible ground for vaccine development due to the fact that virus can induce immune response, so it is not destroying the key immune cells at least in early stage of infection. This factual analysis on the basis of literature survey directed me to focus on screening of SARS-COV2 Spike, Envelop, Matrix and virus specific intracellular proteins for development of vaccine and immunotherapy strategy with my research and development organization. In the first stage of the vaccine development process, the computer-based modeling of screened 900 amino acid containing peptides [selected from total 1281 amino acid containing SARS-COV2 Spike glycoprotein Chain A] with molecular docking experiments is proposed for identification of binding affinity with human class II antigen presenting marker determinant HLA-DR1 as well as immune responder Toll-like receptor 8 (TLR8). The findings enlighten the viral Spike glycoprotein antigen(s) as vaccine candidate.

BRIEF SUMMARY OF THE INVENTION

The proposition presented six epitope sequences from SARS-COV2 Spike glycoprotein, Chain A molecule. The entire 1281 amino acid containing SARS-COV2 Spike glycoprotein Chain A is selected from NCBI protein database. The truncated 60 amino acid sequences were further analyzed on their structures and construction of protein database (PDB) sequence. These PDB sequences were further analyzed for their binding ability to human class II antigen presentation determining marker HLA-DR1 primarily. The same sequences are analyzed for their binding ability to human TLR 8, human ACE2 and anti-SARS-COV2 neutralizing antibody by using computer modeling and molecular docking experimentations. It has been found by computer modeling experiments that the 60 amino acids containing Spike peptides show binding affinity to HLA-DR1 domain D, E and A. The six short peptides of length 19-29 amino acids within 60 amino acids sequences are found to bind with HLA-DR1. The hydrophobicity values of these peptides range from +6.11 to 26.83 kcal/mol. These six peptides use 15-21 amino acid internal sequence to identify human TLR8.

BRIEF DESCRIPTION OF THE SEVERAL VIEWS OF DRAWING(S)

The identification of five truncated peptides from first 900 amino acid sequences of SARS-COV2 Spike glycoprotein Chain A (1281 amino acids) (NCBI Accession ID: 6VXX_A; GI: 1820436168)

TABLE 1

Identification of amino acid sequences in SARS-COV2 Spike glycoprotein show binding affinity with HLA-DR1

| SARS-COV2 spike chain A peptides (amino acid sequences)† | Truncated SARS-COV2 Spike peptide Chain A# | Amino acid sequence of Spike peptides binding with HLA-DR1† (N-terminal is at Left hand side; C-terminal is at Right hand side) |
|---|---|---|
| peptideA:1-60 Met1-Lys60 | Met9-Cys34 (26) | MPALLSLVSLLSVLLMGCVAETGTQC SEQ ID: 1 |
| peptideB:121-180 Arg121-Ser180 | Lys132-Leu160 (29) | KTQSLLIVNNATNVVIKVCEFQFCNDPFL SEQ ID: 2 |
| Peptide C:241-300 Ala 241-Glu 300 | Ala241-His264 | ALEPLVDLPIGINITRFQTLLALH SEQ ID: 3 |

TABLE 1-continued

Identification of amino acid sequences in SARS-COV2 Spike glycoprotein show binding affinity with HLA-DR1

| SARS-COV2 spike chain A peptides (amino acid sequences)† | Truncated SARS-COV2 Spike peptide Chain A# | Amino acid sequence of Spike peptides binding with HLA-DR1‡ (N-terminal is at Left hand side; C-terminal is at Right hand side) |
|---|---|---|
| peptideD:481-540 Lys481-Phe540 | Ser488-Asn506 (19) | STEIYQAGSTPCNGVEGFN SEQ ID : 4 |
| peptideE:601-660 Leu601-Asn660 | Cys609-Thr637 (29) | CSFGGVSVITPGTNTSNQVAVLYQDVNCT SEQ ID: 5 |
| peptideF:841-900 Leu841-Thr900 | Asp849-Phe874 (26) | DAGFIKQYGDCLGDIAARDLICAQKF SEQ ID: 6 |

†The peptides are selected from SARS-COV2 Spike glycoprotein chain A (1281 amino acids) (NCB1 Accession ID: 6VXX_A; GI: 1820436168).
#Number of amino acids in the sequences is shown in parenthesis.
‡The amino acid sequences are derived from initially selected 60 amino acid Spike peptides† tested for their binding affinity with HLA-DR1(PDB: 1AQD) by using computer modeling and molecular docking experiments

TABLE 2

Identification of amino acid sequences in SARS-COV2 Spike glycoprotein show binding affinity with human Toll-like Receptor 8 (TLR 8)
#The domains of amino acid sequences show binding affinity with human TLR 8 (PDB: 3W3L).

| SARS-COV2 truncated Spike peptide binds with HLA-DR1 | Spike peptide amino acid sequence binding with human TLR84# | Spike peptide epitope amino acid sequence binding with TLR8* |
|---|---|---|
| Met9-Cys34 (n = 26) | Met 9-Leu 22 (n = 14) | **MPALLSLVSLLSVL**LMGCVAETGTQC SEQ ID: 7 |
| Lys132-Leu160 (n = 29) | Leu 129-Asn 156 (n = 28) | KTQSLLIVNNATNVVIKVCEFQFCNDPFL **LDSKTQSLLIVNNATNVVIKVCEFQFCN** SEQ ID: 8 |
| Ala241-His264 (n = 24) | Leu 245-Leu 260 (n = 16) | ALEP**LVDLPIGINITRFQTL**LALH SEQ ID: 9 |
| Ser488-Asn506 (n = 19) | Asp 486-Thr497 (n = 12) | STEIYQAGSTPCNGVEGFN **DISTEIYQAGST** SEQ ID: 10 |
| Cys609-Thr637 (n = 29) | Cys 609-Leu 630 (n = 22) | **CSFGGVSVITPGTNTSNQVAVL**YQDVNCT SEQ ID: 11 |
| Asp849-Phe874 (n = 26) | Asp849-Cys870 (n = 22) | **DAGFIKQYGDCLGDIAARDLIC**AQKF SEQ ID: 12 |

The number of interacting amino acids is mentioned within parenthesis.
*The Spike peptide epitope sequences interacting with human TLR 8 are highlighted within the amino acid domain which shows binding affinity with HLA-DR1.

FIGURES AND DRAWINGS

The interaction between proposed SARS-COV2 Spike glycoprotein derived peptide epitope sequences with HLA-DR1 and human TLR 8 are tested by molecular docking experiments using AutoDock Tools (NIH). The colored plates are presented as figures in PDF format as evidence of observations.

FIG. 1. SARS-COV2 Spike peptide A (Metl-Lys60) interacts to bind with HLA-DR1 A, D and E domains via 26 amino acid peptide Met9-Cys34.

Figure 2:
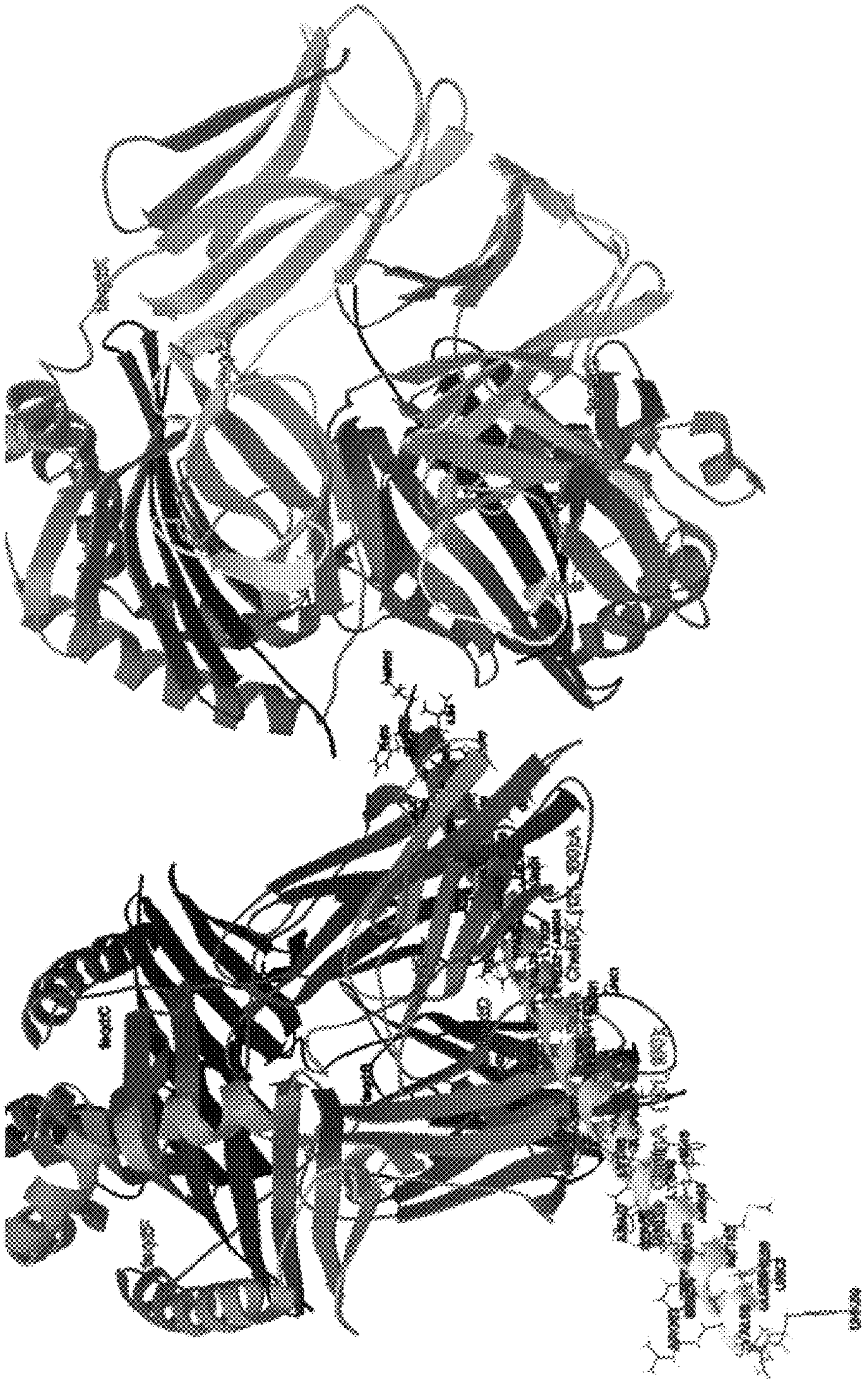

FIG. 2. SARS-COV2 Spike peptide B (Arg121-Ser180) interacts to bind with HLA-DR1 D and E domains via 29 amino acid peptide Lys132-Leu160.

Figure 3:
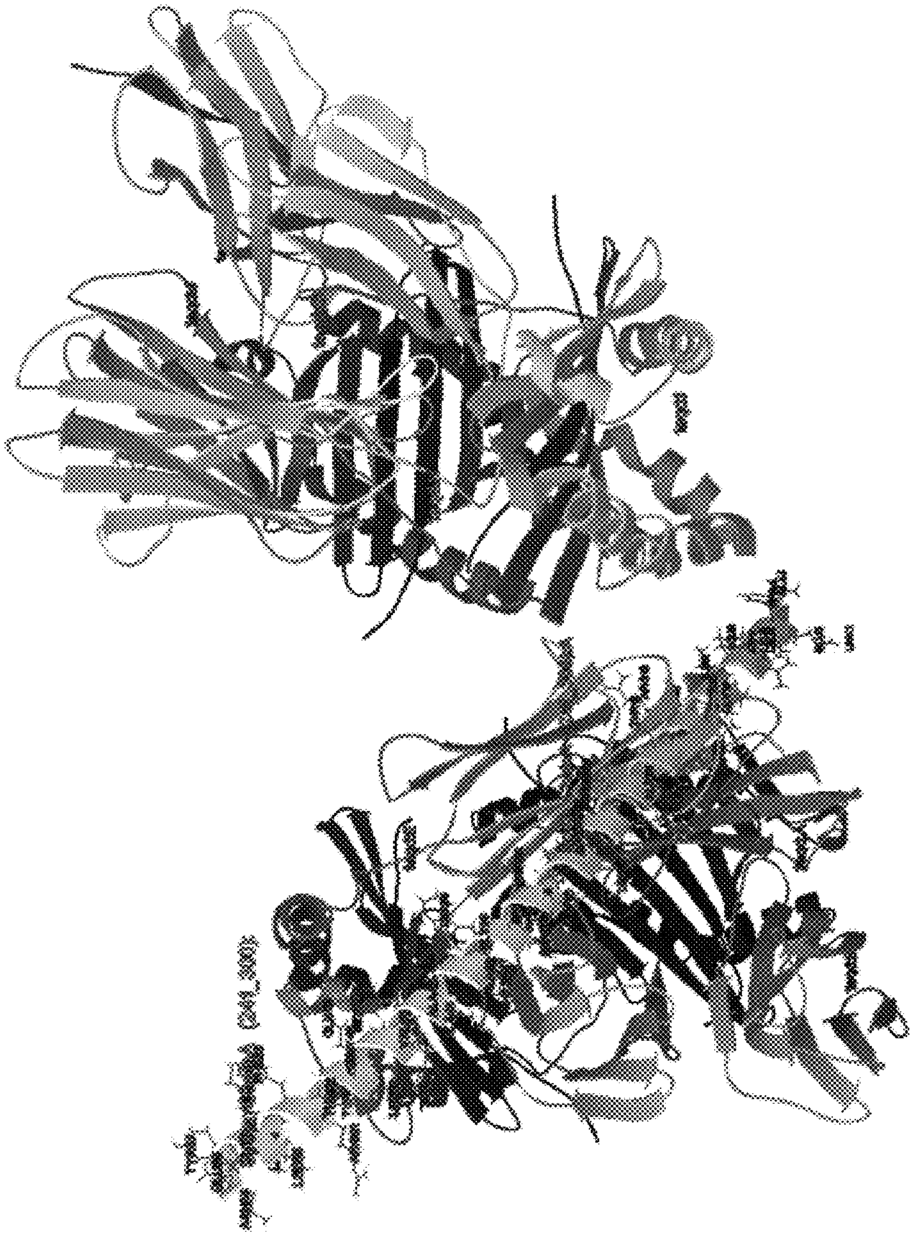

FIG. 3. SARS-COV2 Spike peptide C (Ala241-Glu300) interacts to bind with HLA-DR1 A and D domains via 24 amino acid peptide Ala241-His264.

Figure 4:
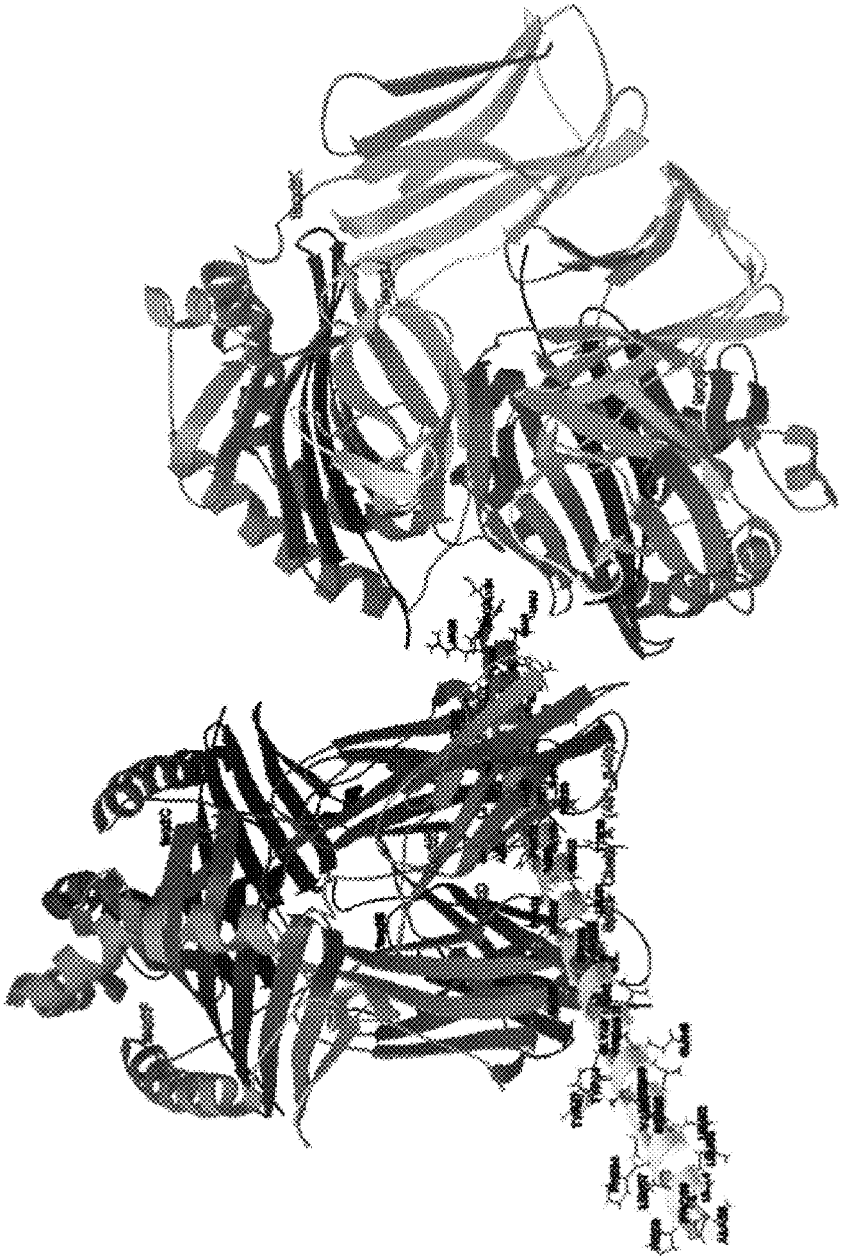

FIG. 4. SARS-COV2 Spike peptide D (Lys481-Phe540) interacts to bind with HLA-DR1 A and D domains via 19 amino acid peptide Ser488-Asn506.

Figure 5:
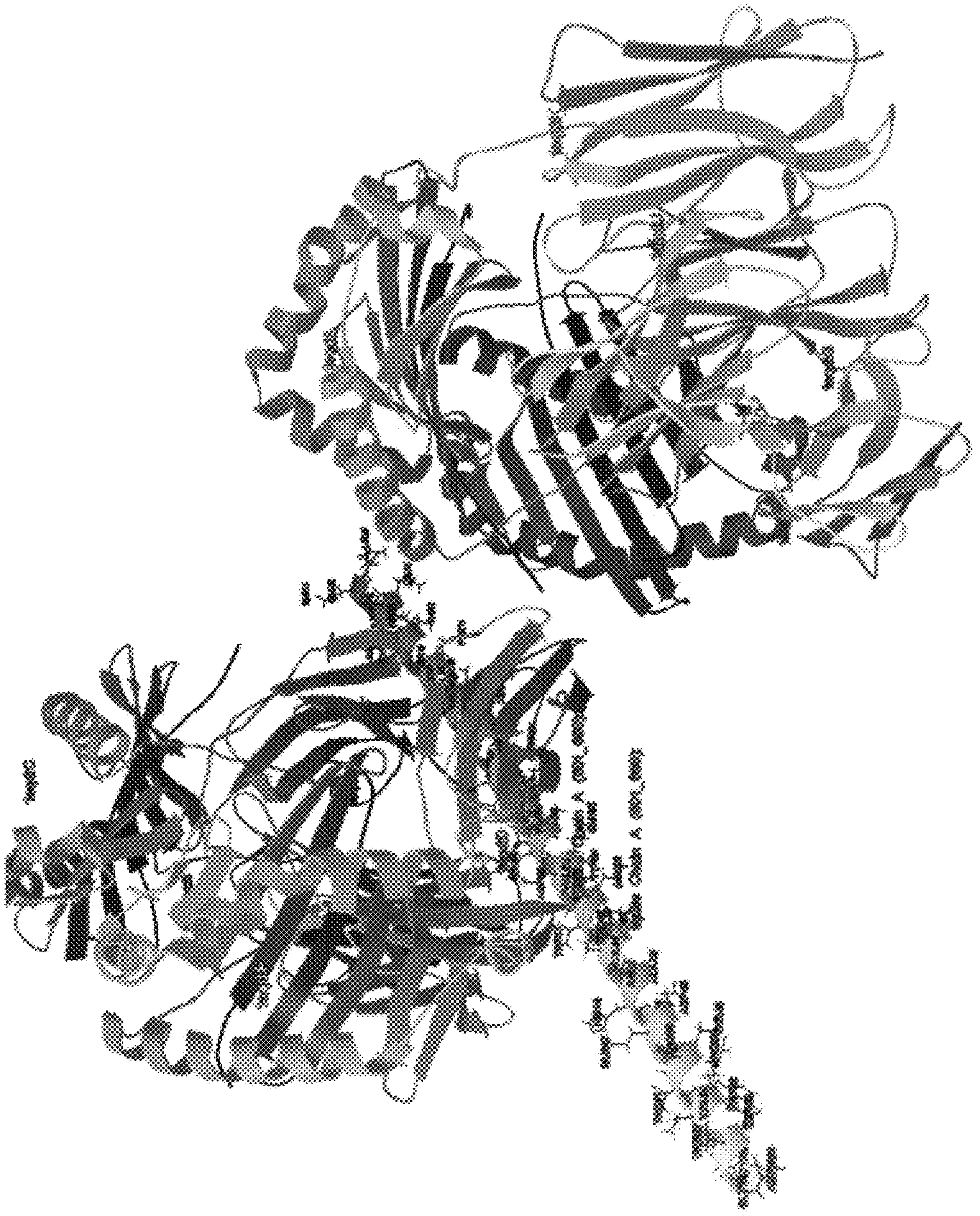

FIG. 5. SARS-COV2 Spike peptide E (Leu601-Asn660) interacts to bind with HLA-DR1 A, D and E domains via 29 amino acid peptide Cys609-Thr637.

Figure 6:
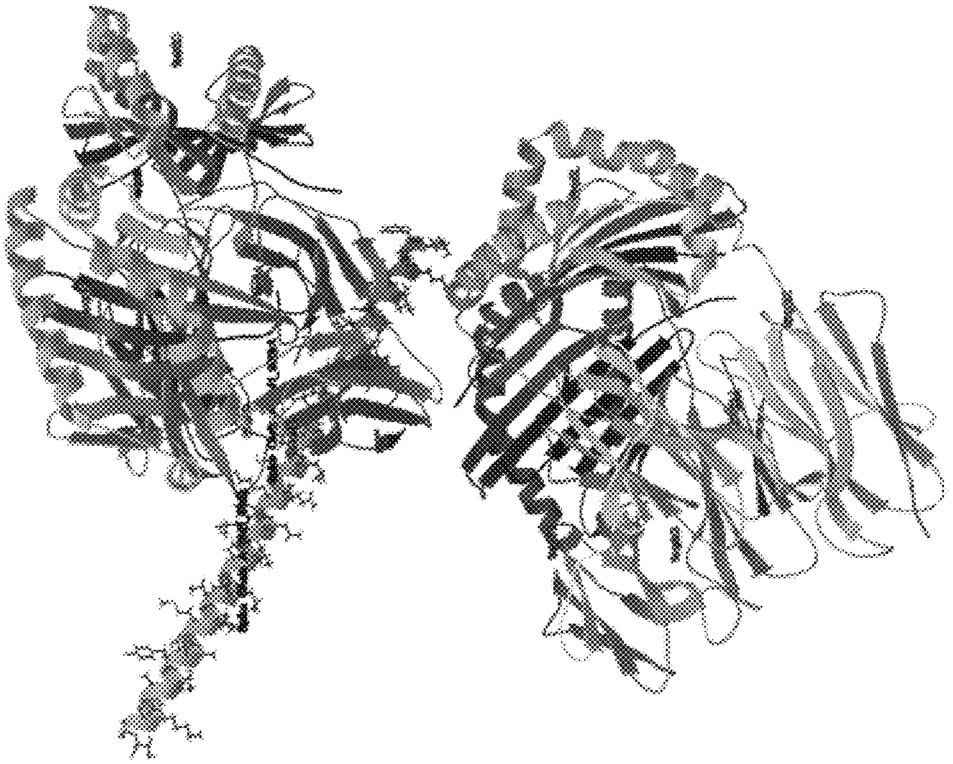

FIG. 6. SARS-COV2 Spike peptide F (Leu841-Thr900) interacts to bind with HLA-DR1 D and E domains via 26 amino acid peptide Asp849-Phe874.

Figure 7:

FIG. 7. SARS-COV2 Spike peptide A (Metl-Lys60) interacts to bind with Human Toll-like Receptor 8 (TLR8) G-domain via 14 amino acid peptide Met9-Leu22.

Figure 8:

FIG. 8. SARS-COV2 Spike peptide B (Arg121-Ser180) interacts to bind with Human Toll-like Receptor 8 (TLR8) G-domain via 28 amino acid peptide Leu129-Asn156.

Figure 9:
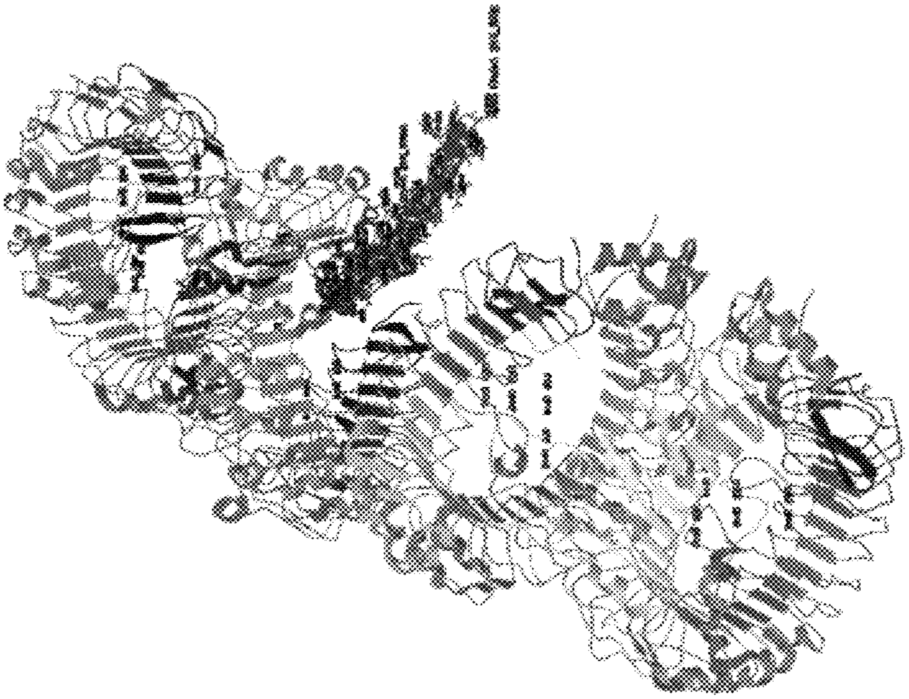

FIG. 9. SARS-COV2 Spike peptide C (Ala241-Glu300) interacts to bind with human Toll-like Receptor 8 (TLR8) G-domain via 16 amino acid peptide Leu245-Leu260.

Figure 10:
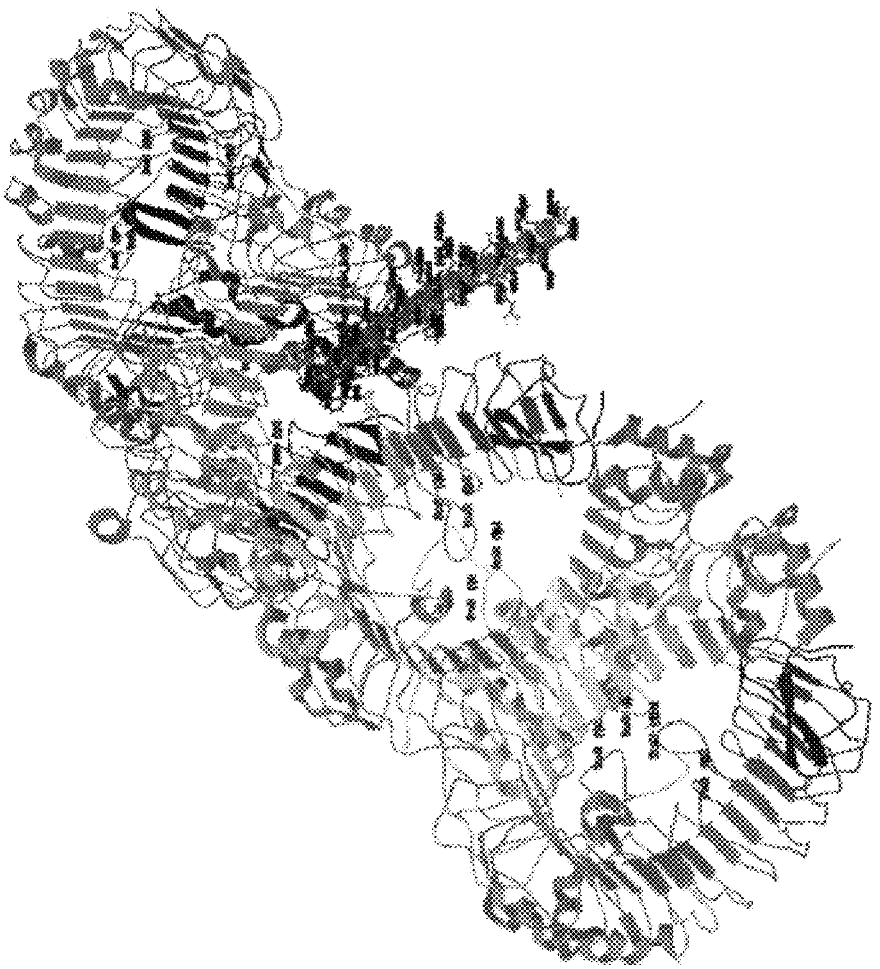

FIG. 10. SARS-COV2 Spike peptide D (Lys481-Phe540) interacts to bind with human Toll-like Receptor 8 (TLR8) G-domain via 12 amino acid peptide Asp486-Thr497.

Figure 11:
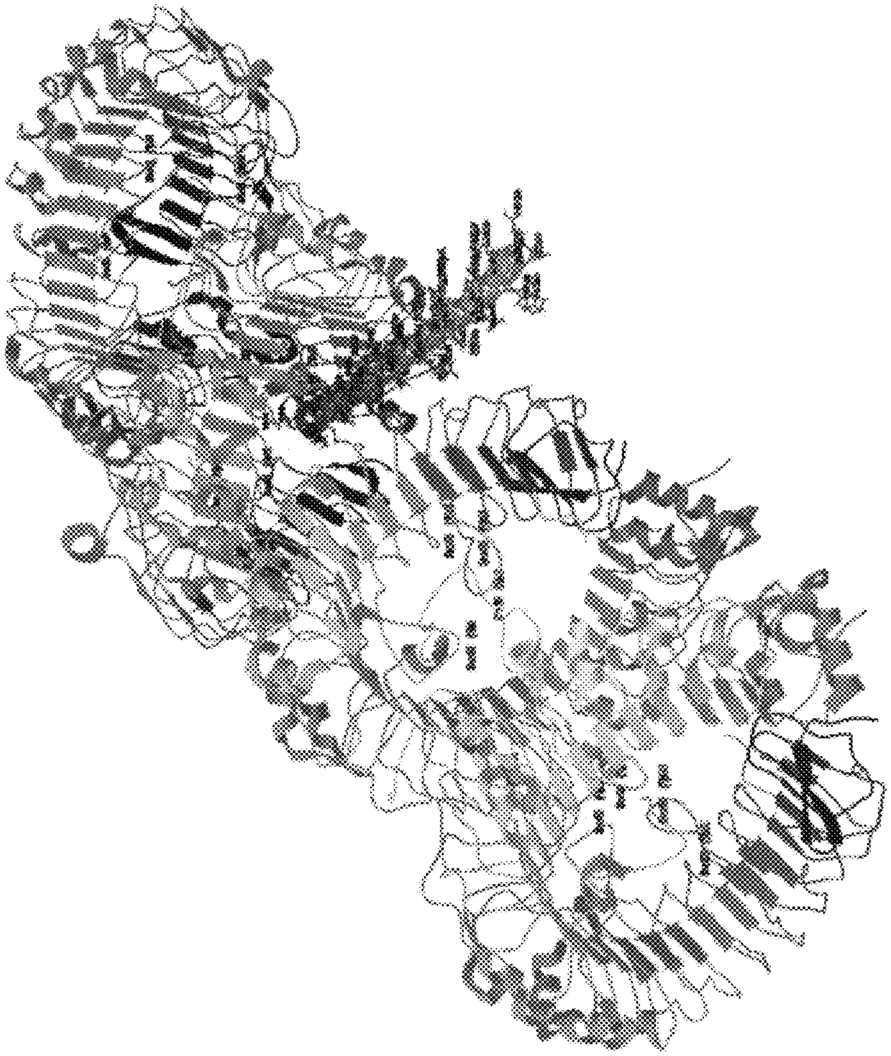

FIG. 11. SARS-COV2 Spike peptide E (Leu601-Asn660) interacts to bind with human Toll-like Receptor 8 (TLR8) G-domain via 22 amino acid peptide Cys609-Leu630.

Figure 12:
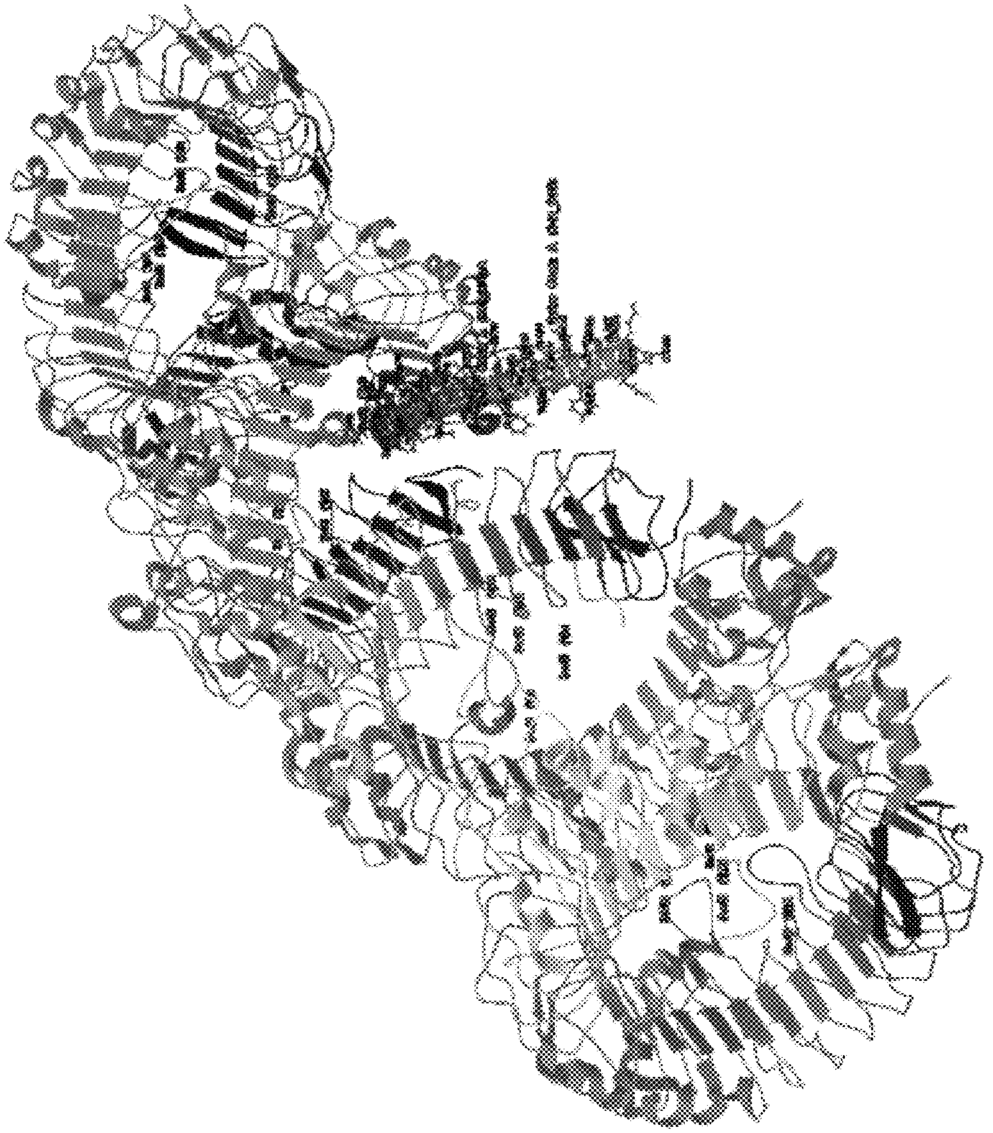

FIG. 12. SARS-COV2 Spike peptide F (Leu841-Thr900) interacts to bind with human Toll-like Receptor 8 (TLR8) G-domain via 22 amino acid peptide Asp849-Cys870.

DETAILED DESCRIPTION OF THE INVENTION

The invention is the identified peptide sequences from SARS-COV2 Spike glycoprotein (NCBI Accession ID: 6VXX_A; GI: 1820436168). These peptide sequences are analyzed by computer modeling and molecular docking experiments for their binding ability and interaction profile with (a) human class II antigen presentation marker determinant HLA-DR1 and, (b) Human Toll-like Receptor protein TLR8. The good-fit profile of antigen as epitope with antigen presenting marker determinant HLA is a requirement for initiation of protective immune response in immunocompetent hosts. Therefore, the assessment of interaction profile between antigen specific epitopes and HLA-DR1 is critical for development of vaccine and immunotherapy.

The Spike glycoprotein (S-protein) of SARS-COV2 is critical for attachment of virus with ACE2 protein. The ACE2 is found to express in upper and lower respiratory tract, lungs, kidneys. The identified first set of sixty amino acid Spike peptides (Table 1) do not exhibit any binding affinity with ACE2 protein [PDB: 6M1D (MMDB: 185057)]. These sixty amino acid spike peptides have been tested for identification of their binding profile with anti-SARS-COV2 human neutralizing antibody C105 (PDB: 6XCA) by using computer modeling and docking experiments. No binding was detected. However, these spike peptides are allowed to dock on human ACE2 protein (PDB: 3KBH) and anti-SARS-COV2 antibody (PDB: 7BWJ). The computer modeling experiments show binding of identified Spike peptide epitopes with ACE2 (3KBH) and anti-SARS antibody (7BWJ). The analysis is continuing at this particular part.

These Spike peptides demonstrate good-fit binding with HLA-DR1 (PDB: 1AQD) and human TLR8 (PDB: 3W3L) at particular domain. Therefore, these identified SARS-COV2 Spike peptides are considered as multi-epitope viral antigens which has ability to induce hosts' immune system and present antigen as part of protective immunity independent of ACE2 attachment. These viral Spike protein derived epitopes can be used as purified or subunit vaccine with less or no side effects as compared with attenuated or inactivated virus particle immunization.

Experimental Procedure

The experiments to identify Spike peptide epitope sequences follow the steps mentioned below.

Step I. Selection of SARS-COV2 Spike glycoprotein sequence from NCBI protein database. The sequence of Spike protein, Chain A with 1281 amino acids (Accession ID: 6VXX_A; GI: 1820436168) is selected for analysis Step II. The sequence is analyzed for its uniqueness by Blastp in NCBI analysis system.

Step III. The SARS-COV2 Spike protein aligned sequences has been selected for further experimentation. Each of these aligned sequences are 60 amino acids peptide (Subjt1 till Subjt 1261 for Query1 till Query1261 in compositional matrix adjustment and Alignment through Blastp.

Step IV. These 60 amino acid peptides are selected in a first phase from Subjct1-60 till Subjct 841-900.

The peptides are analyzed in Avogadro chemistry-based software for construction of PDB sequence. All amino acids are uploaded as its L-configuration and helix conformation.

Step V. The PDB sequence of the 60 amino acid Spike peptides are allowed to dock on HLA-DR1 protein structure (PDB: 1AQD) by using AutoDock Tools. The Spike peptide sequences are reconstructed in its ball and peg model with secondary alpha helical structure when they are allowed to dock on HLA-DR1.

Step VI. The binding nature and amino acids in binding domain of Spike peptides are analyzed from HLA-DR1-Spike peptide association complex from every rotational angle. It is noted that, unassociated proteins will appear in a completely separated domain without any overlap in their interacting chemical structures in computer modeling (Table 1,2; Figures and Drawings 1-6).

Step VII. The amino acid sequence in Spike peptide attached with HLA-DR1 (1AQD) D, E or A domains are recorded. It shows six Spike peptides with number of amino acids 19-29 form complex with HLA-DR1 amino acid sequences: Arg100 to Asp159; Arg100-Pro127; Pro96-Glu137; Arg100-Asp159 in predominantly D and E domains but involvement of A domain is also noted in association complex between Spike peptide and HLA-DR1 (Figures and Drawings 1-6).

Step VIII. These 19-29 amino acid domains of six Spike peptides are analyzed for their physical parameters. The hydrophobicity values are calculated by PepDraw software for each peptide and found a range between +6.11 to +26.83 kcal/mol. The corresponding domain of isoelectric pH of these peptides show in mind to strong acidic range as pH domains are within 3 to 6.13. The ratio of polar to nonpolar amino acid peptides are calculated from the 19-29 amino acids containing Spike peptides. It shows a range between 0.6 to 1 in most of these peptides except two peptides which show the value in the range of 2-2.4 indicating higher polar amino acids in peptides.

Step IX. On the basis of computer modeling and molecular docking experiments, the 19-29 amino acid domains of six viral Spike peptides are digitally confirmed as multi-epitope peptides with ability to bind HLA-DR1.

Step X. In next set of experiments, these 19-29 amino acid sequences are allowed to dock on human TLR8 protein (PDB: 3W3L). The association of Spike peptide amino acids with human TLR8 protein domain G has been analyzed and recorded in Table 2 (the highlighted amino acid sequences)

and in Figures and Drawings 7-12. The analysis shows overlapping peptide sequences of amino acid range 12-22 (Table 2) form associated binding complex with TLR 8 domain-G.

Step XI. The confirmation of Spike peptide epitope sequences for HLA-DR1 and human TLR8 is found within 12 to 22 amino acid sequences overlapped with 19-29 amino acid sequences.

The combinations between 12-22 amino acids including overlap and repeat sequence to generate 5 peptide epitope constructs are within range of 792 (12C 5) to 225 (22C 5) constructs.

SEQUENCE LISTING

| Sequence Number | Title/Subtitle | Page Number |
|---|---|---|
| 1 | Title of invention. Short title, contact address, phone, e-mail | 1 |
| 2 | Cross References | 2-5 |
| 3 | Statement of Federally sponsored research or development | 6 |
| 4 | Names and parties to a joint research agreement | |
| 5 | Reference to a sequence listing | 8 |
| 6 | Background of Invention | 9-10 |
| 7 | Brief summary of Invention | 11 |
| 8 | Brief description of several views of drawings | 12-16 |
| 9 | Detail description of invention | 17-21 |
| 10 | A Claim or Claims | 22 |

-continued

| Sequence Number | Title/Subtitle | Page Number |
|---|---|---|
| 11 | Abstract of disclosures | 23 |
| 12 | Sequence listing | 24 |
| Figures/ drawings/ | FIGS. 1 to 12 (Separate PDF file submitted) | |

New Experiment to Determine Immunogenic Nature of the Identified Spike Peptides of SARS-COV2

Identified Spike peptide epitopes demonstrate T lymphocyte dominant immunogenic characteristics in respect to binding pattern(s) of the epitope(s) to HLA-DRB1alleles 03:01; 07:01 and 15:01 in human population.

The epitope analysis tools for human population (Immune Epitope Database: IEDB) are used to determine immunogenic nature of the identified Spike peptides. We found 16 epitope peptides (each 9 amino acid sequence) with variable level of immunogenicity. As per IEDB combined score value (IEDB combined score is defined combination of HLA binding and immunogenicity scores incorporating T cell receptor: TCR recognition), the lower values indicate higher capacity to be recognized by TCR; thus, low value is more immunogenic; the higher the values are lesser to nonimmunogenic. The individual percentile rank is provided for HLA-DRB1 alleles which indicate, lower percentile rank is related to lower IEDB combined score of epitopes.

A new Table (Table 3) is incorporated in this non provisional application with new results showing medical importance of the Spike epitopes.

TABLE 3

Identified Spike peptide epitopes from SARSCOV2 differentially bind with HLADRB1 alleles and show CD4 dominant immunogenicity

| Spike peptide epitope[≠] | Core peptide[‡] | IEDB combined score′ | HLADR B1:03:01 | HLADR B1:07:01 | HLADR B1:15:01 |
|---|---|---|---|---|---|
| MPALLSLVSLLSVLLM | **LVSLLSVLL**, | 52.20664, | 30, | 4.9, | 6.4, |
| GCVAETGTQC | **LLSVLLMGC**, | 56.00644, | 30, | 8.4, | 6.4, |
| (Met9-Cys34) | LMGCVAETG | 71.46056 | 55 | 69 | 37 |
| KTQSLLIVNNATNVVIK | **TQSLLIVNN**, | 38.7404, | 13, | 23, | 13, |
| VCEFQFCNDPFL | LIVNNATNV, | 54.00504, | 30, | 29, | 33, |
| (Lys132-Leu160) | VIKVCEFQF | 69.2004 | 32 | 30 | 50 |
| ALEPLVDLPIGINITRFQ | LEPLVDLPI, | 62.25884, | 38, | 36, | 42, |
| TLLALH | IGINITREQ, | 59.76052, | 35, | 21, | 49, |
| (Ala241-His264) | **ITRFQTLLA** | 49.76564 | 34 | 13 | 3.6 |
| STEIYQAGSTPCNGVEG | IYQAGSTPC | 74.21128 | 80 | 41 | 42 |
| FN | | | | | |
| (Ser488-Asn506) | | | | | |
| CSFGGVSVITPGTNTSN | SVITPGTNT, | 85.12596 | 76, | 65, | 79, |
| QVAVLYQDVNCT | NTSNQVAVL, | 81.10484 | 74, | 68, | 84, |
| (Cys609-Thr637) | **VAVLYQDVN** | 69.64284 | 51 | 80 | 47 |
| DAGFIKQYGDCLGDIA | GFIKQYGDC | 64.5746 | 87, | 72, | 16, |
| RDLICAQKF | YGDCLGDIA | 78.5712 | 39, | 75, | 79, |
| (Asp849-Phe874) | **IARDLICAQ** | 67.74728 | 12 | 47 | 75 |

[≠]The SARS-COV2 Spike peptides with multiple epitopes are identified . These peptides bind with HLA DR1. The number of amino acids in the peptides show their location in Spike protein sequence (Accession ID: 6VXX_A). [†]Overlapping domains of CD4 immunogenic core peptides present in the identified peptides analyzed by using IEDB resource tools (NIAID, NIH).

[‡]The core peptide sequences are assessed for CD4 immunogenicity by IEDB combined method used for CD4 immunogenicity score. [†]IEDB combined score is a combination of HLA binding and immunogenicity prediction scores incorporating TCR recognition. The low value indicates higher capacity to be recognized by TCR. Low value is more immunogenic; higher values are non-immunogenic. The individual percentile ranks are provided for HLADRB1 alleles B1:03:01, B1:07:01, B1:15:01 (IEDB consensus score is 20.0).

The invention claimed is:

1. A SARS-COV2 Spike peptide consisting of any one of the amino acid sequences selected from the group of SEQ ID Numbers 7; 9; 10; 11; 12 where the peptide is a candidate for vaccine development and monoclonal antibodies for immunotherapy.

2. A composition comprising at least one SARS-COV2 Spike peptide consisting of a peptide selected from the group of SEQ ID Numbers 7; 8; 9; 10; 11; 12 where the composition can be used as multiepitope antigens to generate polyclonal antibodies and activate T cell immune responses to reduce severity of SARS-COV2 reinfection or recurring SARS-COV2 infection.

* * * * *

SEQUENCE LISTING

<160> NUMBER OF SEQ ID NOS: 28

<210> SEQ ID NO 1
<211> LENGTH: 26
<212> TYPE: PRT
<213> ORGANISM: SARSCOV2

<400> SEQUENCE: 1

Met Pro Ala Leu Leu Ser Leu Val Ser Leu Leu Ser Val Leu Leu Met
1 5 10 15

Gly Cys Val Ala Glu Thr Gly Thr Gln Cys
20 25

<210> SEQ ID NO 2
<211> LENGTH: 29
<212> TYPE: PRT
<213> ORGANISM: SARSCOV2

<400> SEQUENCE: 2

Lys Thr Gln Ser Leu Leu Ile Val Asn Asn Ala Thr Asn Val Val Ile
1 5 10 15

Lys Val Cys Glu Phe Gln Phe Cys Asn Asp Pro Phe Leu
20 25

<210> SEQ ID NO 3
<211> LENGTH: 24
<212> TYPE: PRT
<213> ORGANISM: SARSCOV2

<400> SEQUENCE: 3

Ala Leu Glu Pro Leu Val Asp Leu Pro Ile Gly Ile Asn Ile Thr Arg
1 5 10 15

Phe Gln Thr Leu Leu Ala Leu His
20

<210> SEQ ID NO 4
<211> LENGTH: 19
<212> TYPE: PRT
<213> ORGANISM: SARSCOV2

<400> SEQUENCE: 4

Ser Thr Glu Ile Tyr Gln Ala Gly Ser Thr Pro Cys Asn Gly Val Glu
1 5 10 15

Gly Phe Asn

<210> SEQ ID NO 5
<211> LENGTH: 29
<212> TYPE: PRT
<213> ORGANISM: SARSCOV2

<400> SEQUENCE: 5

Cys Ser Phe Gly Gly Val Ser Val Ile Thr Pro Gly Thr Asn Thr Ser
1 5 10 15

Asn Gln Val Ala Val Leu Tyr Gln Asp Val Asn Cys Thr
20 25

<210> SEQ ID NO 6
<211> LENGTH: 26
<212> TYPE: PRT
<213> ORGANISM: SARSCOV2

<400> SEQUENCE: 6

-continued

```
Asp Ala Gly Phe Ile Lys Gln Tyr Gly Asp Cys Leu Gly Asp Ile Ala
1               5                   10                  15

Ala Arg Asp Leu Ile Cys Ala Gln Lys Phe
            20                  25


<210> SEQ ID NO 7
<211> LENGTH: 14
<212> TYPE: PRT
<213> ORGANISM: SARSCOV2

<400> SEQUENCE: 7

Met Pro Ala Leu Leu Ser Leu Val Ser Leu Leu Ser Val Leu
1               5                   10


<210> SEQ ID NO 8
<211> LENGTH: 28
<212> TYPE: PRT
<213> ORGANISM: SARSCOV2

<400> SEQUENCE: 8

Leu Asp Ser Lys Thr Gln Ser Leu Leu Ile Val Asn Asn Ala Thr Asn
1               5                   10                  15

Val Val Ile Lys Val Cys Glu Phe Gln Phe Cys Asn
            20                  25


<210> SEQ ID NO 9
<211> LENGTH: 16
<212> TYPE: PRT
<213> ORGANISM: SARSCOV2

<400> SEQUENCE: 9

Leu Val Asp Leu Pro Ile Gly Ile Asn Ile Thr Arg Phe Gln Thr Leu
1               5                   10                  15


<210> SEQ ID NO 10
<211> LENGTH: 12
<212> TYPE: PRT
<213> ORGANISM: SARSCOV2

<400> SEQUENCE: 10

Asp Ile Ser Thr Glu Ile Tyr Gln Ala Gly Ser Thr
1               5                   10


<210> SEQ ID NO 11
<211> LENGTH: 22
<212> TYPE: PRT
<213> ORGANISM: SARSCOV2

<400> SEQUENCE: 11

Cys Ser Phe Gly Gly Val Ser Val Ile Thr Pro Gly Thr Asn Thr Ser
1               5                   10                  15

Asn Gln Val Ala Val Leu
            20


<210> SEQ ID NO 12
<211> LENGTH: 22
<212> TYPE: PRT
<213> ORGANISM: SARSCOV2

<400> SEQUENCE: 12

Asp Ala Gly Phe Ile Lys Gln Tyr Gly Asp Cys Leu Gly Asp Ile Ala
1               5                   10                  15

Ala Arg Asp Leu Ile Cys
```

20

<210> SEQ ID NO 13
<211> LENGTH: 9
<212> TYPE: PRT
<213> ORGANISM: SARSCOV2

<400> SEQUENCE: 13

Leu Val Ser Leu Leu Ser Val Leu Leu
1 5

<210> SEQ ID NO 14
<211> LENGTH: 9
<212> TYPE: PRT
<213> ORGANISM: SARSCOV2

<400> SEQUENCE: 14

Leu Leu Ser Cys Leu Leu Met Gly Cys
1 5

<210> SEQ ID NO 15
<211> LENGTH: 9
<212> TYPE: PRT
<213> ORGANISM: SARSCOV2

<400> SEQUENCE: 15

Leu Met Gly Cys Val Ala Glu Thr Gly
1 5

<210> SEQ ID NO 16
<211> LENGTH: 9
<212> TYPE: PRT
<213> ORGANISM: SARSCOV2

<400> SEQUENCE: 16

Thr Gln Ser Leu Leu Ile Val Asn Asn
1 5

<210> SEQ ID NO 17
<211> LENGTH: 9
<212> TYPE: PRT
<213> ORGANISM: SARSCOV2

<400> SEQUENCE: 17

Leu Ile Val Asn Asn Ala Thr Asn Val
1 5

<210> SEQ ID NO 18
<211> LENGTH: 9
<212> TYPE: PRT
<213> ORGANISM: SARSCOV2

<400> SEQUENCE: 18

Val Ile Lys Val Cys Glu Phe Gln Phe
1 5

<210> SEQ ID NO 19
<211> LENGTH: 9
<212> TYPE: PRT
<213> ORGANISM: SARSCOV2

<400> SEQUENCE: 19

Leu Glu Pro Leu Val Asp Leu Pro Ile
1 5

-continued

<210> SEQ ID NO 20
<211> LENGTH: 9
<212> TYPE: PRT
<213> ORGANISM: SARSCOV2

<400> SEQUENCE: 20

Ile Gly Ile Asn Ile Thr Arg Phe Gln
1 5

<210> SEQ ID NO 21
<211> LENGTH: 9
<212> TYPE: PRT
<213> ORGANISM: SARSCOV2

<400> SEQUENCE: 21

Ile Thr Arg Phe Gln Thr Leu Leu Ala
1 5

<210> SEQ ID NO 22
<211> LENGTH: 9
<212> TYPE: PRT
<213> ORGANISM: SARSCOV2

<400> SEQUENCE: 22

Ile Tyr Gln Ala Gly Ser Thr Pro Cys
1 5

<210> SEQ ID NO 23
<211> LENGTH: 9
<212> TYPE: PRT
<213> ORGANISM: SARSCOV2

<400> SEQUENCE: 23

Ser Val Ile Thr Pro Gly Thr Asn Thr
1 5

<210> SEQ ID NO 24
<211> LENGTH: 9
<212> TYPE: PRT
<213> ORGANISM: SARSCOV2

<400> SEQUENCE: 24

Asn Thr Ser Asn Gln Val Ala Val Leu
1 5

<210> SEQ ID NO 25
<211> LENGTH: 9
<212> TYPE: PRT
<213> ORGANISM: SARSCOV2

<400> SEQUENCE: 25

Val Ala Val Leu Tyr Gln Asp Val Asn
1 5

<210> SEQ ID NO 26
<211> LENGTH: 9
<212> TYPE: PRT
<213> ORGANISM: SARSCOV2

<400> SEQUENCE: 26

Gly Phe Ile Lys Gln Tyr Gly Asp Cys
1 5

<210> SEQ ID NO 27

-continued

```
<211> LENGTH: 9
<212> TYPE: PRT
<213> ORGANISM: SARSCOV2

<400> SEQUENCE: 27

Tyr Gly Asp Cys Leu Gly Asp Ile Ala
1               5


<210> SEQ ID NO 28
<211> LENGTH: 9
<212> TYPE: PRT
<213> ORGANISM: SARSCOV2

<400> SEQUENCE: 28

Ile Ala Arg Asp Leu Ile Cys Ala Gln
1               5
```